US012678621B2

(12) United States Patent
Goroszeniuk et al.

(10) Patent No.: US 12,678,621 B2
(45) Date of Patent: Jul. 14, 2026

(54) ELECTRODE

(71) Applicant: REMEDIUS LIMITED, London (GB)

(72) Inventors: Teodor Goroszeniuk, London (GB);
Christopher Chan, London (GB)

(73) Assignee: REMEDIUS LIMITED, London (GB)

( * ) Notice: Subject to any disclaimer, the term of this
patent is extended or adjusted under 35
U.S.C. 154(b) by 496 days.

(21) Appl. No.: 17/629,655

(22) PCT Filed: Jul. 15, 2020

(86) PCT No.: PCT/EP2020/070025
§ 371 (c)(1),
(2) Date: Jan. 24, 2022

(87) PCT Pub. No.: WO2021/013654
PCT Pub. Date: Jan. 28, 2021

(65) Prior Publication Data
US 2022/0249841 A1    Aug. 11, 2022

(30) Foreign Application Priority Data

Jul. 22, 2019    (GB) ...................................... 1910452

(51) Int. Cl.
*A61N 1/36*        (2006.01)
*A61N 1/04*        (2006.01)
(52) U.S. Cl.
CPC ....... *A61N 1/36021* (2013.01); *A61N 1/0476*
(2013.01); *A61N 1/0496* (2013.01); *A61N*
*1/36034* (2017.08)
(58) Field of Classification Search
CPC .. A61N 1/0456; A61N 1/0476; A61N 1/0496;
A61N 1/36021; A61N 1/36034
See application file for complete search history.

(56) References Cited

U.S. PATENT DOCUMENTS

| | | | |
|---|---|---|---|
| 5,395,398 A | 3/1995 | Rogozinski | |
| 5,449,378 A | 9/1995 | Schouenborg | |

(Continued)

FOREIGN PATENT DOCUMENTS

| | | | |
|---|---|---|---|
| EP | 2314345 A1 | 4/2011 | |
| GB | 2417688 A | 3/2006 | |

(Continued)

OTHER PUBLICATIONS

Jan. 7, 2020, Search Report issued in Great Britain Patent Application No. GB1910452.0.

(Continued)

*Primary Examiner* — Jennifer Pitrak McDonald
*Assistant Examiner* — Shreya Anjaria
(74) *Attorney, Agent, or Firm* — Oliff PLC

(57)        ABSTRACT

A device, system and method for the delivery of electrical stimulation for the treatment of acute or chronic pain and/or for the improvement of body function. There is described a neuromodulation electrode device including a substrate having a skin-facing surface and an electrode having at least one convex active surface projecting from the skin-facing surface of substrate for applying an electrical stimulation signal. A conductive gel layer having an electrode portion overlies the convex active surface(s) of the electrode. The substrate is formed of a conductive gel or the conductive gel layer further includes a substrate portion overlying the skin-facing surface of the substrate. The device further includes an isolating frame surrounding the perimeter of the electrode to provide electrical isolation between the electrode and the conductive gel substrate or from the substrate portion of the conductive gel layer.

19 Claims, 3 Drawing Sheets

(56) References Cited

U.S. PATENT DOCUMENTS

| | | | |
|---|---|---|---|
| 6,907,294 B2 | 6/2005 | Andino et al. | |
| 9,308,363 B2 | 4/2016 | Goroszeniuk et al. | |
| 2006/0206162 A1* | 9/2006 | Wahlstrand | A61N 1/0502 607/46 |
| 2007/0150008 A1 | 6/2007 | Jones et al. | |
| 2008/0269833 A1 | 10/2008 | Scott et al. | |
| 2009/0048642 A1 | 2/2009 | Goroszeniuk | |
| 2010/0228113 A1* | 9/2010 | Solosko | A61N 1/048 600/382 |
| 2011/0196256 A1 | 8/2011 | Inui et al. | |
| 2013/0053933 A1 | 2/2013 | Inui et al. | |
| 2014/0316505 A1* | 10/2014 | Yanaki | A61N 1/36034 607/139 |
| 2015/0012079 A1* | 1/2015 | Goroszeniuk | A61N 1/0484 607/148 |
| 2018/0296822 A1 | 10/2018 | Schroeder et al. | |

FOREIGN PATENT DOCUMENTS

| | | | |
|---|---|---|---|
| GB | 2435217 B | 9/2011 | |
| GB | 2518929 A | 4/2015 | |
| GB | 2521240 A | 6/2015 | |
| GB | 2571919 A | 9/2019 | |
| JP | 2007-530124 A | 11/2007 | |
| WO | 2007/083275 A1 | 7/2007 | |
| WO | 2018/081819 A1 | 5/2018 | |
| WO | 2018/136999 A1 | 8/2018 | |

OTHER PUBLICATIONS

Oct. 14, 2020, International Search Report issued in International Patent Application No. PCT/EP2020/070025.

Oct. 14, 2020, Written Opinion issued in International Patent Application No. PCT/EP2020/070025.

* cited by examiner

ELECTRODE

FIELD OF THE DISCLOSURE

This invention relates to devices, systems and methods for the delivery of electrical stimulation for the treatment of acute or chronic pain and/or for the improvement of body function.

BACKGROUND

It is known that the application of a mild electrical current through a patient's skin can reduce pain and improve body function e.g. improve digestive function. Such nerve stimulation—or neuromodulation—has been used to help relieve a wide range of ailments including migraines, arthritic pain, muscular pain and neuropathic pain.

Devices used to apply such electrical stimulation include hand-held devices for at-home use by patients. The known devices include sticky electrode patches applied to the skin in the general vicinity of the pain and connected to a power supply. One problem with these known devices is that they are unfocussed and only apply the stimulation to the upper layers of the skin. They are thus unable to provide a focussed and suitably penetrative stimulation depth to target deeper nerves.

To try and provide for a more targeted and deeper penetration of the current, devices have been developed which incorporate electrodes having a domed or ball-like surface that can be pressed into the skin. Such domed/ball electrodes are typically provided only on hand-held probes.

Patients have reported discomfort caused by the pressure of the hard-rounded end of the domed/ball electrodes of the hand held probes. Skin irritation can also arise after prolonged use. To ameliorate these problems, probes having a softer coating e.g. formed of hydrogel have been developed. Such hand-held probes can be uncomfortable to maintain in position, especially if longer application times are required and/or if the body area requiring treatment is not easily accessible.

There is a desire to provide an improved device/system for neuromodulation for the treatment of acute or chronic pain and/or for the improvement of body function, which provides increased comfort and convenience for the user and which maximises the targeted penetration of the electrical stimulation.

SUMMARY

Accordingly, in a first aspect, there is provided a neuromodulation electrode device comprising:

a substrate having a skin-facing surface;

an electrode having at least one convex active surface projecting from the skin-facing surface of substrate for applying an electrical stimulation signal; and a conductive gel layer having an electrode portion overlying the convex active surface(s) of the electrode;

wherein the substrate is formed of a conductive gel or the conductive gel layer further comprises a substrate portion overlying the skin-facing surface of the substrate; and wherein the device further comprises an isolating frame extending around the perimeter of the electrode to provide electrical isolation between the electrode and the conductive gel substrate or from the substrate portion of the conductive gel layer.

By providing a conductive gel layer to the active surface (s) of the electrode, and either a conductive gel substrate or a conductive gel layer substrate portion over the skin-facing surface of the substrate, the comfort of the device against the wearer's skin is significantly increased. Furthermore, the conductive gel layer may reduce any risk of burn injury to the patient. The gel or gel-coated substrate can be used to comfortably affix and maintain the position of the device without the user having to hold it in place—this makes longer application times and inaccessible treatment areas easier to manage for the user. The isolating frame concentrates/focusses and isolates the electrical stimulation through the electrode portion of the conductive gel layer. Without the isolating frame, the inventors found that the electrical stimulation was applied across the whole extent of the conductive gel substrate or conductive gel layer. This attenuation of the electrical stimulation was found to significantly decrease effectiveness in the treatment of pain and improvement of body function. Thus provision of the isolating frame has thus been shown to provide better penetration of the electrical stimulus to the body.

In some embodiments, the substrate is formed of a conductive gel. The conductive gel may be the same or different to the conductive gel of the conductive gel layer.

Where the substrate is formed of conductive gel, there may be a backing layer formed on the surface of the (conductive gel) substrate opposing the skin-facing surface. The backing layer is preferably non-conductive (an electrical insulator).

The backing layer may be a textile backing layer (e.g. a woven or knitted textile fabric layer). In other embodiments, the backing layer may be formed of plastics material. The backing layer may be a silicone rubber.

In other embodiments, the substrate may be formed of non-gel material e.g. a non-conductive plastics (e.g. silicone rubber) or textile material. In these embodiments, the conductive gel layer further comprises a substrate portion that overlies the substrate.

The skin-facing surface of the substrate or the substrate portion of the conductive gel layer may be adhesive. This facilitates attachment and position maintenance of the device on the skin of the patient. It also ensures a firm pressure of the active surface of the electrode into the patient's skin. The adhesive properties of the conductive gel used to form the substrate or to form the substrate portion of the conductive gel layer may be utilised to provide attachment to the patient.

Ideally a conductive gel having reusable adhesive properties is used to form the substrate/substrate portion of the conductive gel layer to allow the device to be reused.

The backing layer or the non-gel substrate may be a stiff and/or self-supporting layer/substrate but pliable to conform to the body part to which the device is applied. It may be pre-formed into a curved profile for application to a specific body part.

In other embodiments, the backing layer or the non-gel substrate may comprise a thermo-formable or curable (e.g. air or chemically curable) material so as to assume a shape that it will retain in use. It can thus be pre-shaped over the site to be treated, and then heated or otherwise treated in order to achieve the desired shape or form.

The backing layer/non-gel substrate may also be used with or be provided with an attachment element such as a strap or band to assist in attaching it firmly to the desired position on a patient. The strap/band may conveniently be secured by means of a hook and loop connection (e.g. Velcro®) so that in use, the device can be held firmly against the skin of a patient.

The isolating frame electrically isolates the electrode (and the electrode portion of the conductive gel layer) from the conductive gel substrate or from the electrode portion of the conductive gel layer.

If the non-gel substrate is conductive, the isolating frame will also electrically isolate the electrode (and the electrode portion of the conductive gel layer) from the non-gel substrate.

The isolating frame may have a width of between 2 and 20 mm i.e. it will provide a non-conductive spacing from the electrode of between 2 and 20 mm.

In some embodiments, the isolating frame is an isolating annulus. The isolating annulus has an inner radius (adjacent the electrode) and an outer radius (adjacent the substrate). The radial spacing between the inner radius and outer radius may be between 2 and 20 mm.

In some embodiments, the isolating annulus is an isolating ring formed of a non-conductive material, e.g. a non-conductive plastics material.

In other embodiments, the isolating frame/annulus is an isolating gap e.g. an isolating gap between the electrode portion and substrate portion of the conductive gel layer.

The electrode is generally formed of a conductive material such as a conductive metal material. It may be formed of a plastic material with a conductive e.g. metallic coating.

The electrode has as least one convex stimulating surface. The electrode may have at least one domed, hemispherical or parabolic stimulating surface.

It may have a circular, triangular, polygonal or square cross section in a plane parallel to the substrate.

In preferred embodiments, the electrode has a single hemispherical stimulating surface with a circular cross-section i.e. the electrode is a domed stud.

Where the electrode has a circular cross-section (e.g. is a domed stud), the effective diameter of the stimulating surface (e.g. at the base of the stimulating surface proximal the substrate) that is in contact with the skin of a patient is typically between 2 mm and 12 mm, though more generally between 6 mm to 10 mm. For use on normal skin (as opposed to mucosal linings) it has been found that an electrode where the diameter of the stimulating surface is between 5 and 10 mm produces best results.

The convex stimulating surface of the electrode typically projects between 3 to 6 mm beyond the skin-facing surface of the substrate.

In some embodiments, the device comprises a plurality of electrodes. In some embodiments, the device comprises an even number of electrodes wherein pairs of electrodes are arranged to receive opposite electrical polarities.

The plurality of electrodes may be mounted in an array or matrix on the substrate. Each of the plurality of electrodes will have a respective isolating frame/annulus.

In some embodiments, the conductive gel layer or the conductive gel substrate is formed of a deformable, electrically-conducting polymeric gel material e.g. a conductive silicone gel polymer.

The conductive gel layer or the conductive gel substrate may be formed of a conductive hydrogel.

A hydrogel is a three-dimensional (3D) network of hydrophilic polymers that can swell in water and hold a large amount of water while maintaining the structure due to chemical or physical cross-linking of individual polymer chains. By definition, water must constitute at least 10% of the total weight (or volume) for a material to be a hydrogel. The conductive hydrogel may contain up to 90 wt % water.

Hydrogels possess a degree of flexibility very similar to natural tissue due to their significant water content. The hydrogel layer is soft and flexible (providing improved comfort to the user) as well as being a good electrical conductor that can also provide a low electrical resistance in contact with skin. Hydrogels are non-irritant to skin and hypoallergenic making them suitable for prolonger contact with skin.

The hydrophilicity of the network is due to the presence of hydrophilic groups such as $-NH_2$, $-COOH$, $-OH$, $-CONH_2$, $-CONH-$, and $-SO_3H$.

Such hydrogels may also adhere lightly to the skin, thus allowing for easy removal and re-use (e.g. up to 10 times). In this specification the term 'hydrogel' refers to any similar gel or substance that may possess such properties.

The conductive gel layer (e.g. the electrode portion) may be between 0.5 to 2.5 mm thick, e.g. between 0.75 to 1 mm thick. Where the conductive gel layer further comprises a substrate portion, the thickness of the substrate portion may match the thickness of the electrode portion.

The conductive gel layer may be provided as a removable and replaceable layer thus allowing the device to be reused indefinitely.

The device may further comprise a protective covering to protect it the conductive gel layer/conductive substrate prior to use and application to a patient's skin and between applications.

In a second aspect, there is provided a neuromodulation system comprising one or more neuromodulation electrode devices according to the first aspect.

Each electrode will have or will be connectable to an electrically-conducting lead for connection to an external electric power supply.

The substrate (where conductive or where further comprising a conductive layer) may additionally, if desired, be connectable (by an electrically conducting lead) to the external power supply permitting it to be used as a grounding electrode or an electrode of the opposite polarity from that of the electrode.

Suitable electric power supplies generate a stimulating signal which may have a frequency from 1 Hz to 10 kHz or higher, and a current of up to 40 mA or higher. Most such generators offer a choice of various wave forms or bursts that will be selected by a professional practitioner.

In a third aspect, there is provided a method for treating chronic or acute pain and/or improving body function comprising application of one or more neuromodulation electrode devices according to the first aspect to an area affected by the pain, and applying a stimulating signal in the range 1 to 10,000 Hz.

The neuromodulation electrode devices should be applied using a firm pressure sufficient to cause indentation of the skin.

The stimulating current is generally chosen within the range 1 to 40 mA, according to the sensitivity of the area to be treated. In some specific instances a higher current may need to be applied.

Various wave forms and wave patterns may be used to stimulate through the electrodes.

The skilled person will appreciate that except where mutually exclusive, a feature or parameter described in relation to any one of the above aspects may be applied to any other aspect. Furthermore, except where mutually exclusive, any feature or parameter described herein may be applied to any aspect and/or combined with any other feature or parameter described herein.

BRIEF DESCRIPTION OF THE DRAWINGS

Embodiments will now be described by way of example only, with reference to the Figures, in which.

DETAILED DESCRIPTION

Aspects and embodiments of the present disclosure will now be discussed with reference to the accompanying figures. Further aspects and embodiments will be apparent to those skilled in the art.

Figure 1:
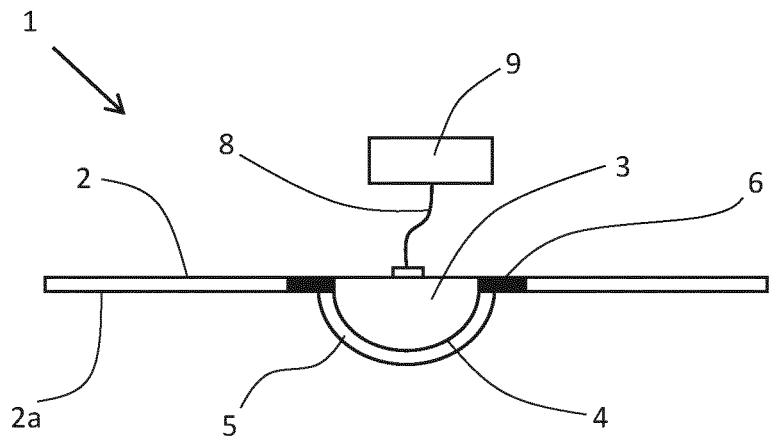
FIG. 1 is a cross-sectional view of a device according to a first embodiment.
Figure 2:
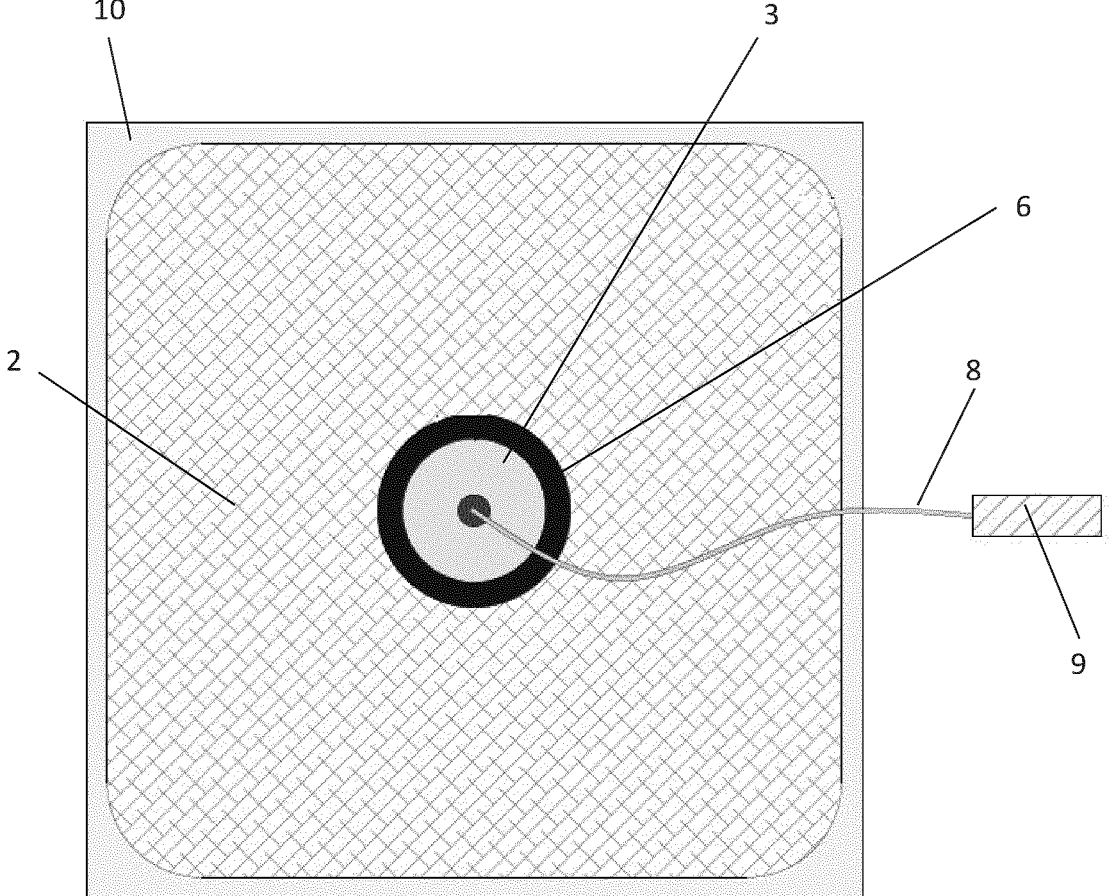
FIG. 2 is a top view of the FIG. 1 embodiment.

FIGS. 1 and 2 show a device 1 comprising a substrate 2 having a skin-facing surface 2a formed of a conductive hydrogel having a thickness of 2 mm. Although not shown, the conductive hydrogel substrate 2 may comprise a backing layer formed of a thermo-formable or curable material that can be moulded to and retained in the shape a body portion to be treated.

The skin-facing surface 2a of the conductive hydrogel substrate 2 is adhesive. Prior to use, the adhesive surface 2a is protected with a protective cover layer 10 (shown in FIG. 2).

The substrate 2 surrounds an electrode 3 having a circular cross-section with a maximum diameter of 17 mm and a depth of 6 mm. The electrode has a domed/hemispherical stimulating surface 4 which is coated with an electrode portion of a conductive hydrogel layer 5 having a thickness of 1 mm.

An isolating annulus comprising an isolating ring 6 of non-conductive material encircles the base of the electrode and electrically isolates the electrode 3 and conductive hydrogel layer 5.

The electrode comprises an electrically conducting lead 8 for connection to a power supply 9.

In use, the device 1 is applied to the patient's skin with the adhesive skin-facing surface 2a of the substrate 2 affixed to the skin such that the active surface 4 of the electrode 3 in indented into the skin. The hydrogel layer 5 helps cushion the skin and increases comfort. The power supply 9 and electrically conducting lead 8 are used to apply a stimulating signal in the range 1 to 10,000 Hz (with a stimulating current within the range 1 to 40 mA) according to the sensitivity of the area to be treated. The signal is focused through the electrode 3 and conductive gel layer 5 and is not attenuated through the hydrogel substrate 2. This has been found to increase the effectiveness of pain reduction and/or body function improvement.

Figure 3:
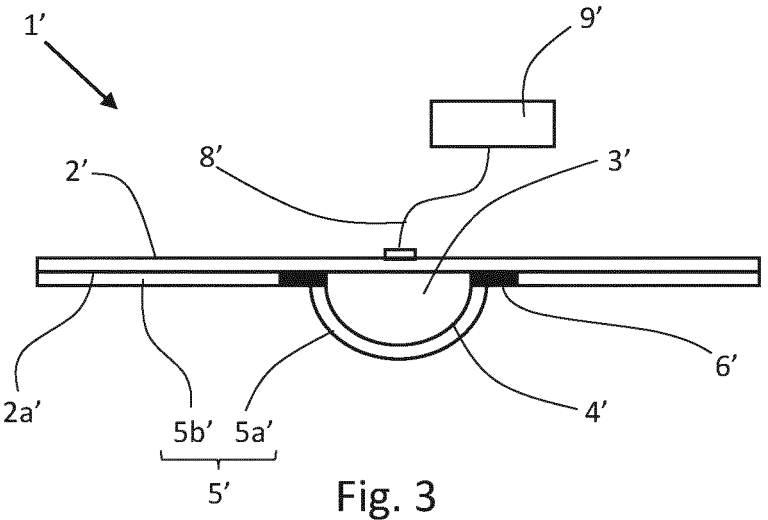
FIG. 3 is a cross-sectional view of a device according to a second embodiment.

FIG. 3 shows an alternative embodiment of a device 1' where the substrate 2' comprises a non-woven textile material and the conductive hydrogel layer 5' comprises an electrode portion 5a' (covering the active surface 4' of the electrode 3') and a substrate portion 5b' (covering the skin-facing surface 2a' of the substrate 2').

The isolating ring 6' electrically isolates the electrode portion 5a' and the substrate portion 5b' from one another.

The electrode portion 5a' of the conductive hydrogel layer 5' is also isolated from the substrate 2'.

The device 1' is used as described above for the first embodiment but with the adhesive substrate portion 5b' of the conductive hydrogel layer 5' affixed to the skin such that the active surface 4' of the electrode 3' in indented into the skin. The signal is focused through the electrode 3' and the electrode portion 5a' of the conductive hydrogel layer 5' and is not attenuated through the substrate portion 5b' of the conductive hydrogel layer 5'.

Figures 4, 5:
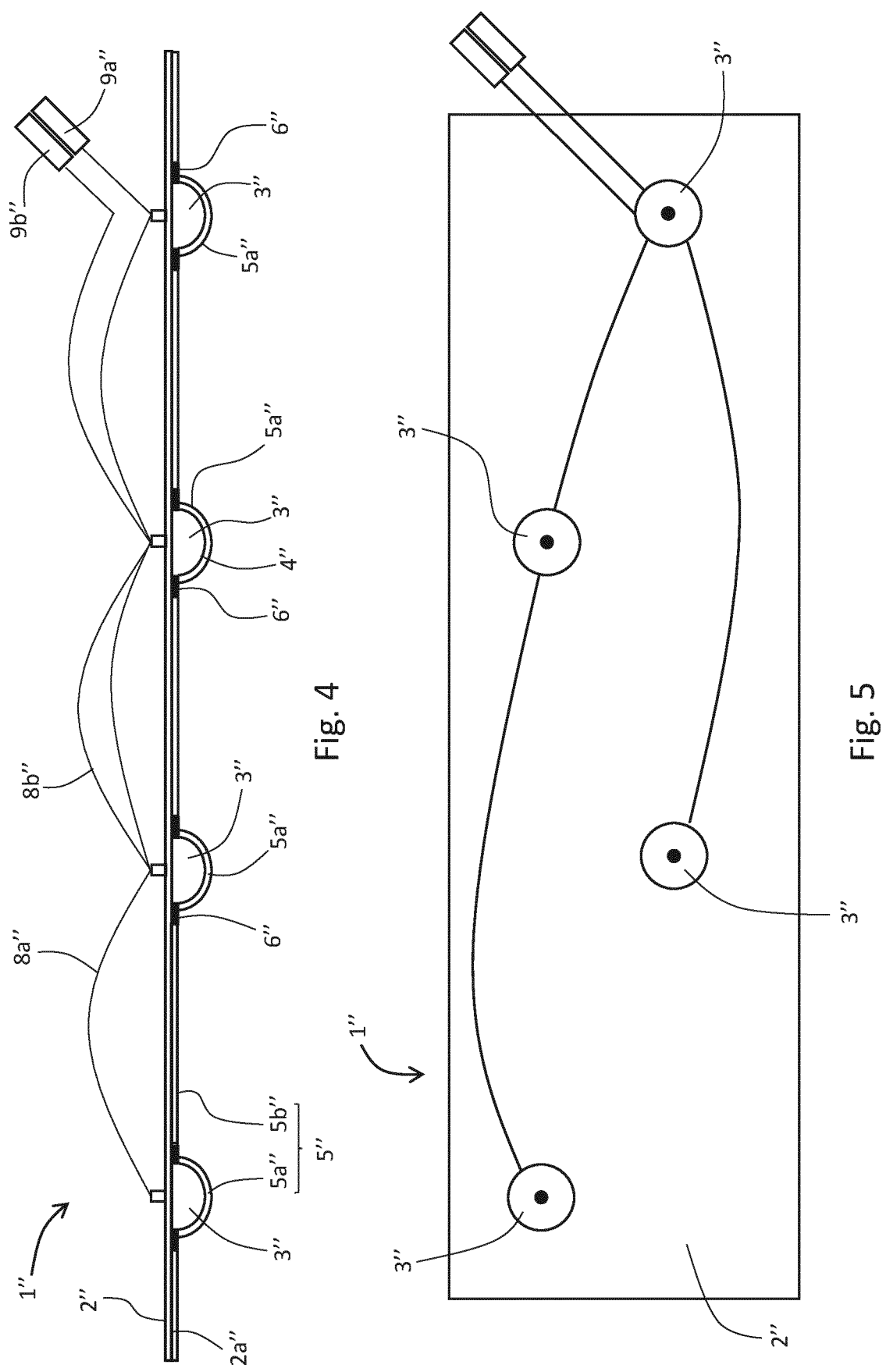
FIG. 4 shows a cross-sectional view of a device according to a third embodiment.
FIG. 5 shows a top view of the FIG. 4 embodiment.

FIGS. 4 and 5 show a third embodiment of the device 1" comprising a plurality of electrodes 3" mounted on a non-conductive substrate 2" and surrounded by a substrate portion 5b" of a conductive hydrogel layer 5". The active surface 4" of each electrode 3" is covered by a respective electrode portion 5a" of the conductive hydrogel layer 5".

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

The invention claimed is:

1. A neuromodulation electrode device comprising:
a substrate having a skin-facing surface;
an electrode having at least one convex active surface projecting from the skin-facing surface of substrate for applying an electrical stimulation signal; and
a conductive gel layer having an electrode portion overlying the convex active surface(s) of the electrode;
wherein the substrate is formed of a conductive gel or the conductive gel layer further comprises a substrate portion overlying and in contact with the skin-facing surface of the substrate and surrounding the electrode; and
wherein the device further comprises an isolating frame extending around the perimeter of the electrode when viewed in a direction perpendicular to the skin-facing surface, wherein:
the isolating frame is between the electrode and the substrate formed of conductive gel when viewed in the direction perpendicular to the skin-facing surface and spaces the electrode apart from the substrate formed of conductive gel such that the electrode is electrically isolated from the substrate formed of the conductive gel, or
the isolating frame is between the electrode and the substrate portion of the conductive gel layer when viewed in the direction perpendicular to the skin-facing surface and spaces the electrode apart from the substrate portion of the conductive gel layer such that the electrode is electrically isolated from the substrate portion of the conductive gel layer.

2. The device according to claim 1 wherein the substrate is formed of conductive gel and further comprises a backing layer formed on the surface of the conductive gel substrate opposing the skin-facing surface.

3. The device of claim 1 wherein the substrate is formed of a non-gel material and the conductive gel layer further comprises a substrate portion that overlies the substrate.

4. The device of claim 3 wherein the electrode portion and substrate portion of the conductive gel layer are of uniform thickness.

5. The device of claim 2 wherein the backing layer is formed of a self-supporting, pliable material, or wherein the substrate is formed of a non-gel material which is a self-supporting, pliable material.

6. The device of claim 2 wherein the backing layer is formed of a thermos-formable or curable material, or wherein the substrate is formed of a non-gel material which is a thermo-formable or curable material.

7. The device of claim 1 wherein the skin-facing surface of the substrate or the substrate portion of the conductive gel layer is adhesive.

8. The device of claim 1 wherein the isolating frame has a width of between 2 and 20 mm.

9. The device of claim 1 wherein the isolating frame is an isolating annulus comprising an isolating ring formed of a non-conductive material or an isolating gap.

10. The device of claim 1 wherein the electrode has a single hemispherical stimulating surface with a circular cross-section.

11. The device of claim 10 wherein the diameter of the electrode is between 2 and 12 mm.

12. The device of claim 1 wherein the convex stimulating surface of the electrode projects between 3 to 6 mm beyond the skin-facing surface of the substrate.

13. The device of claim 1 wherein the device comprises a plurality of electrodes mounted in an array or matrix on the substrate, each of the plurality of electrodes having a respective isolating frame.

14. The device of claim 1 wherein the conductive gel layer or the conductive gel substrate is formed of a conductive hydrogel.

15. A device of claim 1 wherein each of the electrodes and the conductive gel substrate/substrate portion of the conductive gel layer comprises a respective electrically conducting leads for connection to a power source so as to impart a first polarity to the electrode(s) and a second opposite polarity to the conductive gel substrate/substrate portion of the conductive gel layer.

16. A neuromodulation system comprising one or more neuromodulation electrode devices of claim 1 and an external electric power supply.

17. The system according to claim 16 wherein the electric power supply is adapted to generate a stimulating signal having a frequency of from 1 Hz to 10 kH and a current of up to 40 mA.

18. A method for treating chronic or acute pain and/or improving body function comprising application of one or more neuromodulation electrode devices according to claim 1 to an area affected by the pain, and applying a stimulating signal in the range 1 to 10,000 Hz.

19. The device according to claim 1 wherein the electrode portion of the conductive gel layer includes a concave surface facing the electrode and receiving the electrode therein and a convex surface opposing the concave surface and projecting from the substrate formed of the conductive gel or the substrate portion of the conductive gel layer.

\* \* \* \* \*